United States Patent
Chardes et al.

(10) Patent No.: US 10,196,455 B2
(45) Date of Patent: Feb. 5, 2019

(54) NEUREGULIN ALLOSTERIC ANTI-HER3 ANTIBODY

(71) Applicants: INSERM (Institut National de la Sante et de la Recherche Medicale), Paris (FR); Universite de Montpellier, Montpellier (FR); Institut Regional du Cancer de Montpellier, Montpellier (FR)

(72) Inventors: Thierry Chardes, Montpellier (FR); Nadege Gaborit, Rehovot (IL); Christel Larbouret, Montpellier (FR); Andre Pelegrin, Montpellier (FR)

(73) Assignees: INSERM (Institut National de la Sante et de la Recherche Medicale), Paris (FR); Universite de Montpellier, Montpellier (FR); Institut Regional du Cancer de Montpellier, Montpellier (FR)

( * ) Notice: Subject to any disclaimer, the term of this patent is extended or adjusted under 35 U.S.C. 154(b) by 0 days.

(21) Appl. No.: 15/035,129

(22) PCT Filed: Nov. 7, 2013

(86) PCT No.: PCT/IB2013/002733
§ 371 (c)(1),
(2) Date: May 6, 2016

(87) PCT Pub. No.: WO2015/067986
PCT Pub. Date: May 14, 2015

(65) Prior Publication Data
US 2016/0319033 A1    Nov. 3, 2016

(51) Int. Cl.
*C07K 16/00*     (2006.01)
*A61K 39/395*    (2006.01)
*G01N 33/574*    (2006.01)
*C07K 16/32*     (2006.01)
*A61K 39/00*     (2006.01)

(52) U.S. Cl.
CPC ....... *C07K 16/32* (2013.01); *G01N 33/57492* (2013.01); *A61K 2039/505* (2013.01); *A61K 2039/507* (2013.01); *C07K 2317/24* (2013.01); *C07K 2317/30* (2013.01); *C07K 2317/565* (2013.01); *C07K 2317/73* (2013.01); *C07K 2317/732* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

WO    2012156532 A1    11/2012

OTHER PUBLICATIONS

Rudikoff et al, Proc. Natl. Acad. Sci. USA, 79(6):1979-1983, Mar. 1982.*
Colman P. M., Research in Immunology, 145:33-36, 1994.*
MacCallum et al, J. Mol. Biol., 262, 732-745, 1996.*
Lazrek et al., "Anti-HER Domain 1 and 3 Antibodies Reduce Tumor Growth by Hindering HER2.HER3 Dimerization and AKT-Induced MDM2, XIAP, and Fox01 Phosphorylation", NEOPLASIA, Mar. 2013, vol. 15-347.

* cited by examiner

*Primary Examiner* — Mark Halvorson
(74) *Attorney, Agent, or Firm* — W&C IP

(57) ABSTRACT

The present disclosure relates to neuregulin (NRG)-non competitive allosteric anti-human-HER3 antibodies and uses thereof in diagnostic and therapeutic methods.

14 Claims, 8 Drawing Sheets
Specification includes a Sequence Listing.

NEUREGULIN ALLOSTERIC ANTI-HER3 ANTIBODY

FIELD OF THE INVENTION

The present invention relates to neuregulin (NRG)-non competitive allosteric anti-human-HER3 antibodies and uses thereof in diagnostic and therapeutic methods.

BACKGROUND OF THE INVENTION

The human epidermal growth factor receptor ErbB/HER family of receptor tyrosine kinases (RTK) includes four members: EGFR (ErbB1/HER1), HER2 (c-Neu, HER2), HER3 (HER3) and HER4 (HER4). The HER receptors comprise an extracellular glycosylated domain consisting of four structural domains, marked 1 to 4, followed by a transmembrane domain and an intracellular C-terminal part containing a kinase domain for coupling to signalling pathways. Except for HER3, the intracellular region contains a tyrosine kinase activity. Signalling is mediated through ligand-induced receptor dimerization and subsequent phosphorylation that leads to the activation of cytoplasmic signalling pathways. HER2 has no specific ligand because it is naturally under an "active" conformation. The other HER receptors exist as inactive monomers with the molecules folded in such a way to prevent dimerization. Ligand binding to domains 1 and 3 induces major conformational changes ultimately exposing the dimerization loop in domain 2 of the receptor. This exposure of the dimerization loop allows for receptor dimerization.

The HER3 receptor, that has been first described in 1990, is the only HER family member receptor that lacks the intrinsic kinase activity and downstream signalling is achieved through heterodimerization. Thus, the HER3 receptor, as a monomer, is called "non-self" and cannot form homodimers. Binding of the ligand neuregulin (NRG) to HER3 receptor triggers the heterodimerization of HER3 with the others HER family receptors (HER2 preferentially). Within the heterodimer, the HER3 kinase domain acts as an allosteric activator of its HER family partner.

HER3 is implicated in tumorigenesis of various cancers including breast and ovarian cancer (Lee-Hoeflich S T, Cancer Res. 2008; McIntyre E, Breast Cancer Res Treat. 2010; Tanner B, J Clin Oncol. 2006). HER3 expression correlates with tumor progression and reduced patient survival in malignant melanoma and metastases, and is associated with decrease survival in ovary cancer. Importantly, in breast cancer, tumors with low HER2 expression, which are not eligible to Herceptin treatment, often are "programmed" to strongly express HER3 (Smith et al. Br. J. Cancer 2004), and HER2+++ tumors, which become resistant to Herceptin after prolonged treatment, are "re-programmed" to strongly express HER3 (Narayan, Cancer Res. 2009). Cetuximab resistance was also associated with HER3 over-expression in lung cancer (Wheeler, Oncogene 2008) and colorectal carcinomas (Lu Cancer Res 2007), together with dysregulation of EGFR internalization/degradation. Recently, HER3 over-expression was significantly associated with worse metastasis-free survival in colorectal carcinoma (Ho-Pun-Cheung, Int J Cancer 2010). Thus, HER3 over-expression and compensatory signalling through activation of the PI3K/AKT pathway are implicated in the development of resistance to treatment with HER-targeted therapies (antibodies and TKI) (Wheeeler 2008, Lu 2007, Narayan, 2009, Sergina, 2007) but also to treatment with IGFR-targeted therapies (Desbois-Mouthon, Clin Cancer Res 2009) and with chemotherapeutic agents (Kruser, Exp Cell Res 2010).

All these findings suggest that HER3-targeted agents, and in particular antibodies, might help to further understand the role of HER3 signalling in cancers and especially be used as efficient immunotherapeutics.

At present, no therapeutic anti-HER3 antibody is commercialized although the scientific literature strongly emphasizes the interest of targeting HER3 in therapeutic oncology. Two human antibodies are currently under development by Merrimack Pharmaceuticals/Sanofi Aventis (MM-121 antibody; PCT WO2008/100624) and U3 PharmaAG/Daiichi Sankyo/Amgen (U3-1287 or AMG-888; PCT WO2007/077028). MM-121 antibody is involved in a phase I clinical trial in NSCLC and in a phase I/II trial in ER+PR+ HER2– breast cancer. U3-1287 antibody is in phase I in NSCLC in association with Erlotinib. One EGFR/HER3 bispecific antibody MEHD7945A (Genentech; PCT WO2010/108127) is still in research development. One HER2/HER3 bispecific antibody MM-111 (Merrimack Pharmaceuticals; PCT WO2005/117973, WO2006/091209) is involved in phase I/II clinical trials, alone or in combination with trastuzumab or lapatinib, in HER2-amplified breast cancer.

All the above mentioned antibodies block the heregulin-binding site of the HER3 receptor, thus reducing these antibody therapies to ligand-addicted tumors. Targeting HER3 with antibodies that are not directed to the heregulin-binding site of HER3 should make possible to bypass the resistance to targeted therapies or chemotherapy in resistant HER2-amplified breast cancer, to broaden the application field of targeted therapies to HER2low breast cancer, which are currently not eligible for such treatment, or to treat triple-negative breast cancers, which express HER3 and for which no targeted therapy is available yet.

SUMMARY OF THE INVENTION

The present invention relates to neuregulin (NRG)-non competitive allosteric anti-human-HER3 antibodies and uses thereof in diagnostic and therapeutic methods.

DETAILED DESCRIPTION OF THE INVENTION

The inventors have characterized a murine anti-human-HER3 antibody, named 9F7-F11, which has unique specificity to HER3-positive cells in the presence of the ligand neuregulin. The inventors have, in particular, shown that 9F7-F11/HER3 affinity is not inhibited when neuregulin is present (the 9F7-F11 antibody is neuregulin-non competitive), but furthermore, 9F7-F11/HER3 affinity is allosterically increased when neuregulin is present in the environment of HER3-positive cells (9F7-F11 is an allosteric anti-HER3 antibody). The NRG-non competitive allosteric antibody 9F7-F11 inhibits MAPK, AKT and p53 pathways, blocks cell cycle in G1 phase, inhibits cell proliferation and restores apoptosis of tumor cells. This unique antibody 9F7-F11 reduces tumor growth of NRG-addicted pancreatic cancers, and HER2-amplified or triple-negative breast cancers, and is more efficient in combination with HER2-specific antibody pertuzumab than HER2 combination trastuzumab/pertuzumab or HER2 antibodies used alone.

The therapeutic antibody 9F7-F11 would have clinical utility in a broad spectrum of tumors than a ligand-competitive antibody or a ligand-non competitive antibody devoid of allosteric effect, which targeted more restricted mechanisms of HER3 activation. Due to its allosteric effect, the NRG-non competitive antibody 9F7-F11 would be more efficient on ligand-dependent tumors than others antibodies, when neuregulin is secreted by the tumors (autocrine secretion) or by the microenvironmement (paracrine secretion). Due to its allosteric effect, the antibody 9F7-F11 would be more efficient when resistance, mediated by up-regulation of neuregulin, occurs (i.e. cetuximab resistance in colorectal carcinoma). Due to its allosteric effect, 9F7-F11 binding might be improved when receptors are heterodimerized after activation by ligands. Taken together, NRG-non competitive allosteric anti-human HER3 antibody 9F7-F11 may be used to treat conditions where existing therapeutic antibodies are clinically ineffective.

In conclusion, the antibodies of the invention provide the following advantages over the anti-HER3 antibodies described in the prior art:
  they are allosteric antibodies
  they are neuregulin-non competitive
  they provide a broader spectrum of action (both ligand-independent and ligand-dependent cancers)
  they are more efficient on autocrine or paracrine ligand-dependent tumors (due to its allosteric effect)
  they are more efficient when resistance, mediated by up-regulation of HER3 ligands, occurs (ex: resistance to antibodies or TKI, to chemo, to anti-hormone).
  They may be used to treat conditions where existing therapeutic antibodies are clinically ineffective, such as for triple-negative breast cancer, pancreatic cancer, other niches (ex: renal cell carcinoma)

Definitions

The term "neuregulin" has its general meaning in the art and is often used interchangeably with the term "heregulin". The heregulin family includes alpha, beta and gamma heregulins (Holmes et al., Science, 256: 1205-1210 (1992); U.S. Pat. No. 5,641,869; and Schaefer et al. Oncogene 15: 1385-1394 (1997)); neu differentiation factors (NDFs), glial growth factors (GGFs); acetylcholine receptor inducing activity (ARIA); and sensory and motor neuron derived factor (SMDF). For a review, see Groenen et al. Growth Factors 11:235-257 (1994); Lemke, G. Molec. & Cell. Neurosci. 7:247-262 (1996) and Lee et al. Pharm. Rev. 47:51-85 (1995); Falls and D. (2003). "Neuregulins: functions, forms, and signaling strategies." Experimental Cell Research 284(1): 14-30.

The term "HER3" refers to the human HER3 receptor as described in Plowman et al., Proc. Natl. Acad. Sci. USA, 87:4905-4909 (1990); see, also, Kani et al., Biochemistry 44: 15842-857 (2005), Cho and Leahy, Science 297: 1330-1333 (2002)). HER3 is also known as "HER3".

The term "anti-human-HER3 antibody" refers to an antibody directed against human HER3.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody derived the 9F7-F11 antibody, and a CH domain and a CL domain of a human antibody.

According to the invention, the term "humanized antibody" refers to an antibody having variable region framework and constant regions from a human antibody but retains the CDRs of the 9F7-F11 antibody.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

Antibodies of the Invention:

The present invention provides for isolated neuregulin (NRG)-non competitive allosteric anti-HER3 antibodies or fragments thereof. In particular, the inventors have raised a murine anti-HER3 antibody (9F7-F11) producing hybridoma. The inventors have cloned and characterized the variable domain of the light and heavy chains of said mAb 9F7-F11, and thus determined the complementary determining regions (CDRs) domain of said antibody as described in Table 1:

having a sequence selected from the group consisting of SEQ ID NO:6 for L-CDR1, SEQ ID NO:7 for L-CDR2 and SEQ ID NO:8 for L-CDR3.

The monoclonal antibody of the invention, may comprise a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3 and a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

In particular, the invention provides an anti-HER3 monoclonal antibody comprising an heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

In one particular embodiment, the heavy chain variable region of said antibody has the amino acid sequence set forth as SEQ ID NO: 1 and/or the light chain variable region has the amino acid sequence set forth as SEQ ID NO: 5.

In another embodiment, the monoclonal antibody of the invention is a chimeric antibody, preferably a chimeric mouse/human antibody. In particular, said mouse/human chimeric antibody may comprise the variable domains of 9F7-F11 antibody as defined above.

In another embodiment, the monoclonal of the invention is a humanized antibody. In particular, in said humanized antibody, the variable domain comprises human acceptor

TABLE 1 amino acid sequences of VH, VL and CDRs of mAb 9F7-F11

| mAb 9F7-F11 Domains | Sequence |
|---|---|
| VH | EVKLVESGGGLVQPGGSLKLSCAASGFTFSSYTMSWVRQTPEKR LEWVAYISDGGGVTYYPDTIKGRFTISRDNAKNTLYLQMSSLKSE DTAMYYCARDRYGLFAYWGQGTLVTVSA (SEQ ID NO: 1) |
| H CDR1 | GFTFSSYT (SEQ ID NO: 2) |
| H CDR2 | ISDGGGVT (SEQ ID NO: 3) |
| H CDR3 | ARDRYGLFAY (SEQ ID NO: 4) |
| VL | DIVMTQSQKFMSTSVGDRVSITCKASQNVGIAVAWYQQKPGQSP KLLIYSASNRYTGVPDRFTGSGSGTDFTLTISNMQSEDLADYFCQ QYSNYPYTFGGGTKLEIK (SEQ ID NO: 5) |
| L CDR1 | QNVGIA (SEQ ID NO: 6) |
| L CDR2 | SAS (SEQ ID NO: 7) |
| L CDR3 | QQYSNYPYT (SEQ ID NO: 8) |

Therefore, the invention relates to a monoclonal antibody having specificity for HER3, comprising a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3.

The invention also relates to a monoclonal antibody having specificity for HER3, comprising a light chain wherein the variable domain comprises at least one CDR frameworks regions, and optionally human constant domain where present, and non-human donor CDRs, such as mouse CDRs as defined above.

The invention further provides anti-HER3 fragments directed against HER3 of said antibodies which include but are not limited to Fv, Fab, F(ab')2, Fab', dsFv, scFv, sc(Fv)2 and diabodies.

In another aspect, the invention relates to a polypeptide which has a sequence selected from the group consisting of SEQ ID NO: 1, SEQ ID NO:2, SEQ ID NO:3, SEQ ID NO:4, SEQ ID NO:5; SEQ ID NO: 6; SEQ ID NO:7 and SEQ ID NO:8.

Methods of Producing Antibodies of the Invention:

Anti-human-HER3 antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid sequence encoding an antibody according to the invention.

In one particular embodiment, the invention relates to a nucleic acid sequence encoding the VH domain of the antibody obtainable from hybridoma 9F7-F11 or the VL domain of the antibody obtainable from hybridoma 9F7-F11.

In one particular embodiment, the invention relates to a nucleic acid sequence comprising the sequence SEQ ID NO:9.

In one particular embodiment, the invention relates to a nucleic acid sequence comprising the sequence SEQ ID NO:10.

TABLE 2

Nucleic acids of VH and VL domains of mAb 9F7-F11 of the invention

| | |
|---|---|
| VH domain: | GAA GTG AAG CTG GTG GAG TCT GGG GGA GGT TTA GTG CAG CCT GGA GGG TCC CTG AAA CTC TCC TGT GCA GCC TCT GGA TTC ACT TTC AGT AGC TAT ACC ATG TCT TGG GTT CGC CAG ACT CCA GAG AAG AGG CTG GAG TGG GTC GCA TAC ATT AGT GAT GGT GGT GTC ACC TAC TAT CCA GAC ACT ATA AAG GGC CGA TTC ACC ATC TCC AGA GAC AAT GCC AAG AAC ACC CTG TAC CTG CAA ATG AGC AGT CTG AAG TCT GAG GAC ACG GCC ATG TAT TAC TGT GCA AGA GAT AGG TAC GGT CTC TTT GCT TAC TGG GGC CAA GGG ACT CTG GTC ACT GTC TCT GCA (SEQ ID NO: 9) |
| VL domain: | GAC ATT GTG ATG ACC CAG TCT CAA AAA TTC ATG TCC ACA TCA GTA GGA GAC AGG GTC AGC ATC ACC TGC AAG GCC AGT CAG AAT GTG GGT ATT GCT GTA GCC TGG TAT CAA CAG AAA CCA GGA CAA TCT CCT AAA CTA CTG ATT TAC TCG GCA TCC AAT CGG TAC ACT GGA GTC CCT GAT CGC TTC ACA GGC AGT GGA TCT GGG ACA GAT TTC ACT CTC ACC ATC AGC AAT ATG CAG TCT GAA GAC CTG GCA GAT TAT TTC TGC CAG CAA TAT AGC AAC TAT CCG TAC ACG TTC GGA GGG GGG ACC AAG CTG AAA TAA AAC (SEQ ID NO: 10) |

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-

Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

In another particular embodiment, the method comprises the steps of:

(i) culturing the hybridoma 9F7-F11 under conditions suitable to allow expression of 16D3-C1 antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In one particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with human HER3 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with human HER3 with a protease, pepsin. Also, the F(ab')2 can be produced by binding Fab' described below via a thioether bond or a disulfide bond.

The Fab' of the present invention can be obtained treating F(ab')2 which specifically reacts with human HER3 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. No. 5,859,205; U.S. Pat. No. 5,585,089; U.S. Pat. No. 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Accordingly, the invention also provides an antibody comprising a heavy chain wherein the variable domain comprises:
 a H-CDR1 having at least 90% or 95% identity with sequence set forth as SEQ ID NO: 2,
 a H-CDR2 having at least 90% or 95% identity with sequence set forth as SEQ ID NO: 3,
 a H-CDR3 having at least 90% or 95% identity with sequence set forth as SEQ ID NO: 4,
 a L-CDR1 having at least 90% or 95% identity with sequence set forth as SEQ ID NO: 6,
 a L-CDR2 having at least 90% or 95% identity with sequence set forth as SEQ ID NO: 7,
 a L-CDR3 having at least 90% or 95% identity with sequence set forth as SEQ ID NO: 8, and
 that specifically binds to HER3 with substantially the same affinity as an antibody comprising a heavy chain wherein the variable domain comprises SEQ ID NO: 2 for H-CDR1, SEQ ID NO: 3 for H-CDR2 and SEQ ID NO: 4 for H-CDR3 and a light chain wherein the variable domain comprises SEQ ID NO: 6 for L-CDR1, SEQ ID NO: 7 for L-CDR2 and SEQ ID NO: 8 for L-CDR3, and more preferably with substantially the same affinity as the murine anti-HER3 antibody 9F7-F11.

Said antibodies may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscaataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGl for FcγRI, FcγRII, FcγRIII and FcRn have been mapped and variants with improved binding have been described (see Shields, R. L. et al., 2001 J. Biol. Chen. 276:6591-6604, WO2010106180).

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues (eurekainc.com/a&boutus/companyoverview.html). Alternatively, the antibodies of the invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Immunoconjugates:

An antibody of the invention can be conjugated with a detectable label to form an anti-HER3 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-HER3 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-HER3 immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-HER3 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-HER3 immunoconjugates can be detectably labeled by linking an anti-human-HER3 monoclonal antibody to an enzyme. When the anti-HER3-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-human-HER3 monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-human-HER3 monoclonal antibodies that have been conjugated with avidin, streptavidin, and biotin. (See, e.g., Wilchek et al. (eds.), "Avidin-Biotin Technology," *Methods In Enzymology* (Vol. 184) (Academic Press 1990); Bayer et al., "Immunochemical Applications of Avidin-Biotin Technology," in *Methods In Molecular Biology* (Vol. 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

In another aspect, the present invention provides an anti-human-HER3 monoclonal antibody-drug conjugate. An "anti-human-HER3 monoclonal antibody-drug conjugate" as used herein refers to an anti-human-HER3 monoclonal antibody according to the invention conjugated to a therapeutic agent. Such anti-human-HER3 monoclonal antibody-drug conjugates produce clinically beneficial effects on HER3-expressing cells when administered to a subject, such as, for example, a subject with a HER3-expressing cancer, typically when administered alone but also in combination with other therapeutic agents.

In typical embodiments, an anti-human-HER3 monoclonal antibody is conjugated to a cytotoxic agent, such that the resulting antibody-drug conjugate exerts a cytotoxic or cytostatic effect on a HER3-expressing cell (e.g., a HER3-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-human-HER3 monoclonal antibody can be conjugated to a cytotoxic agent such as a chemotherapeutic agent or a toxin (e.g., a cytostatic or cytocidal agent such as, for example, abrin, ricin A, *pseudomonas* exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, *vinca* alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., *Cancer Res.* 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etopside phosphate (VP-16), 5-fluorouracil, gramicidin D, hydroxyurea, idarubicin, ifosfami de, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, *vinca* alkaloids, CC-1065, SN-38 (7-ethyl-10-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, a cytotoxic agent is a conventional chemotherapeutic such as, for example, doxorubicin, paclitaxel, melphalan, *vinca* alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-HER3-expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), *vinca* alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, an anti-human-HER3 monoclonal antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Mono-* clonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.)

Diagnostic Uses:

A further object of the invention relates to an anti-human-HER3 antibody of the invention for diagnosing and/or monitoring a cancer disease associated with HER3 expression. Cancer diseases associated with HER3 expression typically include but are not limited to squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In one particular embodiment, a cancer diagnosed using the methods of the present invention is breast cancer or ovarian cancer. In one particular embodiment, antibodies of the invention are useful for diagnosing breast and ovarian cancer.

In one particular embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as 1123, 1124, In111, Re186, Re188. Antibodies of the invention may be also labelled with a spin label for nuclear magnetic resonance (NMR) imaging (also known as magnetic resonance imaging, mri), such as iodine-123, iodine-131, indium-Ill, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Antibodies of the invention may be useful for staging of cancer diseases associated with HER3 expression (e.g., in radioimaging). For example, antibodies of the invention may be useful for staging a breast or ovarian cancer. They may be used alone or in combination with other breast or ovarian cancer markers, including, but not limited to, HER2, CAl 25, HE4 and mesothelin.

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with HER3 expression, and in one particular embodiment from breast or ovary. Therefore, biological samples encompass clinical samples, cells in culture, cell supernatants, cell lysates, serum, plasma, biological fluid, and tissue samples.

In one particular embodiment, the invention is a method of diagnosing a cancer disease associated with HER3 expression in a subject by detecting HER3 on cells from the subject using the antibody of the invention. In particular, said method of diagnosing may comprise the steps consisting of:

(a) contacting a biological sample of a subject likely to suffer from a cancer disease associated with HER3 expression with an antibody according to the invention in conditions sufficient for the antibody to form complexes with cells of the biological sample that express HER3;

(b) detecting and/or quantifying said complexes, whereby the detection of said complexes is indicative of a cancer disease associated with HER3 expression.

In order to monitor the cancer disease, the method of diagnosing according to the invention may be repeated at different intervals of time, in order to determine if antibody binding to the samples increases or decreases, whereby it is determined if the cancer disease progresses or regresses.

Therapeutic Uses:

Antibodies, fragments or immunoconjugates of the invention may be useful for treating any HER3-expressing cancer. The antibodies of the invention may be used alone or in combination with any suitable agent.

Examples of HER3-expressing cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In one particular embodiment, a cancer treated using the methods of the present invention is breast cancer or ovarian cancer.

Thus, an object of the invention relates to a method for treating a cancer associated with the expression of HER3 comprising administering a subject in need thereof with a therapeutically effective amount of an antibody, fragment or immunoconjugate of the invention.

In some embodiment, the antibodies of the invention are particularly suitable for the treatment of ligand (i.e. NRG) independent cancers and ligand dependent cancers.

In some embodiment, the antibodies of the invention are particularly suitable for the treatment of autocrine or paracrine ligand-dependent tumors (due to its allosteric effect).

In some embodiment, the antibodies of the invention are particularly suitable for the treatment of cancers that are resistant to the treatment with antibodies, tyrosine kinase inhibitors (TKI), chemotherapeutic agents, or anti-hormone agents.

In some embodiment, the antibodies of the invention are particularly suitable for the treatment of cancers selected from the group consisting of triple-negative breast cancer, pancreatic cancer, and renal cell carcinomas.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "patient" or "patient in need thereof" is intended for a human or non-human mammal affected or likely to be affected with cancer associated with the expression of human HER3 cancer associated with the expression of human HER3.

By a "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

In certain embodiments, an anti-human-HER3 monoclonal antibody or antibody-drug conjugate is used in combination with a second agent for treatment of a disease or disorder. When used for treating cancer, an anti-human-HER3 monoclonal antibody or antibody-drug conjugate of the present invention may be used in combination with conventional cancer therapies such as, e.g., surgery, radiotherapy, chemotherapy, or combinations thereof. In certain aspects, other therapeutic agents useful for combination cancer therapy with an anti-HER3 antibody or antibody-drug conjugate in accordance with the present invention include anti-angiogenic agents. In some aspects, an antibody or antibody-drug conjugate in accordance with the present invention is co-administered with a cytokine (e.g., a cytokine that stimulates an immune response against a tumor.

In some other aspects, other therapeutic agents useful for combination therapy include an antagonist of certain factors that are involved in tumor growth such as, for example, EGFR, HER2, or HER4.

In one particular embodiment an anti-human-HER3 monoclonal antibody or antibody-drug conjugate of the present invention is used in combination with an anti-human-HER2 monocolonal antibody, such as Trastuzumab or Pertuzumab.

In some embodiments, an anti-human-HER3 monoclonal antibody or antibody-drug conjugate as described herein is used in combination with a tyrosine kinase inhibitor (TKI). BAY 43-9006 (sorafenib, Nexavar®) and SU11248 (sunitinib, Sutent®) are two such TKIs that have been approved. Other TKIs include, but are not limited to: Imatinib mesylate (Gleevec®, Novartis); Gefitinib (Iressa®, AstraZeneca); Erlotinib hydrochloride (Tarceva®, Genentech); Vandetanib (Zactima®, AstraZeneca), Tipifarnib (Zarnestra®, Janssen-Cilag); Dasatinib (Sprycel®, Bristol Myers Squibb); Lonafarnib (Sarasar®, Schering Plough); Vatalanib succinate (Novartis, Schering AG); Lapatinib (Tykerb®, GlaxoSmithKline); Nilotinib (Novartis); Lestaurtinib (Cephalon); Pazopanib hydrochloride (GlaxoSmithKline); Axitinib (Pfizer); Canertinib dihydrochloride (Pfizer); Pelitinib (National Cancer Institute, Wyeth); Tandutinib (Millennium); Bosutinib (Wyeth); Semaxanib (Sugen, Taiho); AZD-2171 (AstraZeneca); VX-680 (Merck, Vertex); EXEL-0999 (Exelixis); ARRY-142886 (Array BioPharma, AstraZeneca); PD-0325901 (Pfizer); AMG-706 (Amgen); BIBF-1120 (Boehringer Ingelheim); SU-6668 (Taiho); CP-547632 (OSI); (AEE-788 (Novartis); BMS-582664 (Bristol-Myers Squibb); JNK-401 (Celgene); R-788 (Rigel); AZD-1152 HQPA (AstraZeneca); NM-3 (Genzyme Oncology); CP-868596 (Pfizer); BMS-599626 (Bristol-Myers Squibb); PTC-299 (PTC Therapeutics); ABT-869 (Abbott); EXEL-2880 (Exelixis); AG-024322 (Pfizer); XL-820 (Exelixis); OSI-930 (OSI); XL-184 (Exelixis); KRN-951 (Kirin Brewery); CP-724714 (OSI); E-7080 (Eisai); HKI-272 (Wyeth); CHIR-258 (Chiron); ZK-304709 (Schering AG); EXEL-7647 (Exelixis); BAY-57-9352 (Bayer); BIBW-2992 (Boehringer Ingelheim); AV-412 (AVEO); YN-968D1 (Advenchen Laboratories); Midostaurin (Novartis); Perifosine (AEterna Zentaris, Keryx, National Cancer Institute); AG-024322 (Pfizer); AZD-1152 (AstraZeneca); ON-01910Na (Onconova); and AZD-0530 (AstraZeneca).

Pharmaceutical Compositions:

For administration, the anti-human-HER3 monoclonal antibody or antibody-drug conjugate is formulated as a pharmaceutical composition. A pharmaceutical composition comprising an anti-human-HER3 monoclonal antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995).) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits:

Finally, the invention also provides kits comprising at least one antibody of the invention. Kits containing antibodies of the invention find use in detecting HER3 expression, or in therapeutic or diagnostic assays. Kits of the invention can contain an antibody coupled to a solid support, e.g., a tissue culture plate or beads (e.g., sepharose beads). Kits can be provided which contain antibodies for detection and quantification of HER3 in vitro, e.g. in an ELISA or a Western blot. Such antibody useful for detection may be provided with a label such as a fluorescent or radiolabel.

The invention will be further illustrated by the following figures and examples. However, these examples and figures should not be interpreted in any way as limiting the scope of the present invention.

FIGURES

FIG. 1 shows the mutual allosteric effect of mAb 9F7-F11 and NRG for the binding to the HER3 receptor on cells. 9F7-F11 binding to HER3 increases on SKBR3 cells when various concentrations of NRG are added. In contrast antibody A is not affected by NRG binding and antibody B is blocked by NRG binding (Panel A). Inversely, NRG binding to HER3 increases on HER2/HER3-transfected 3T3 fibroblasts when various concentration of mAb 9F7-F11 are added, whereas irrelevant IgG does not affect NRG binding. In contrast, free NRG displaces labelled-NRG for the binding to HER3 (Panel B).

FIG. 2 quantifies the 9F7-F11 affinity to the HER3 receptor with or without NRG. A 6-fold increase in affinity was measured in the presence of NRG (0.47±0.07 nM), with regard to affinity measured in the absence of NRG (2.33±0.30 nM).

EXAMPLE 1: ALLOSTERIC EFFECT OF 9F7-F11 ON HER3 BINDING

One Balb/c mice was injected intraperitoneally with HER2/HER3-transfected NIH 3T3 cell line (around 2×10$^6$ cells), previously stimulated with neuregulin 131 (NRG) to promote HER2/HER3 heterodimer formation. Spleen cells from immunized mice were fused according to the protocol already described (Salhi et al. Biochem. J. 2004) using the myeloma PX63Ag8.653. 10$^5$ fused cells per well were cultured in plates with HAT media for hybridoma selection. After 12 days post fusion, the hybridoma supernatant screening was performed by ELISA using the protein HER3-Fc as antigen. In control, screenings will be done simultaneously with discriminating antigens HER2-Fc and the Fc fragment alone.

Figure 1:
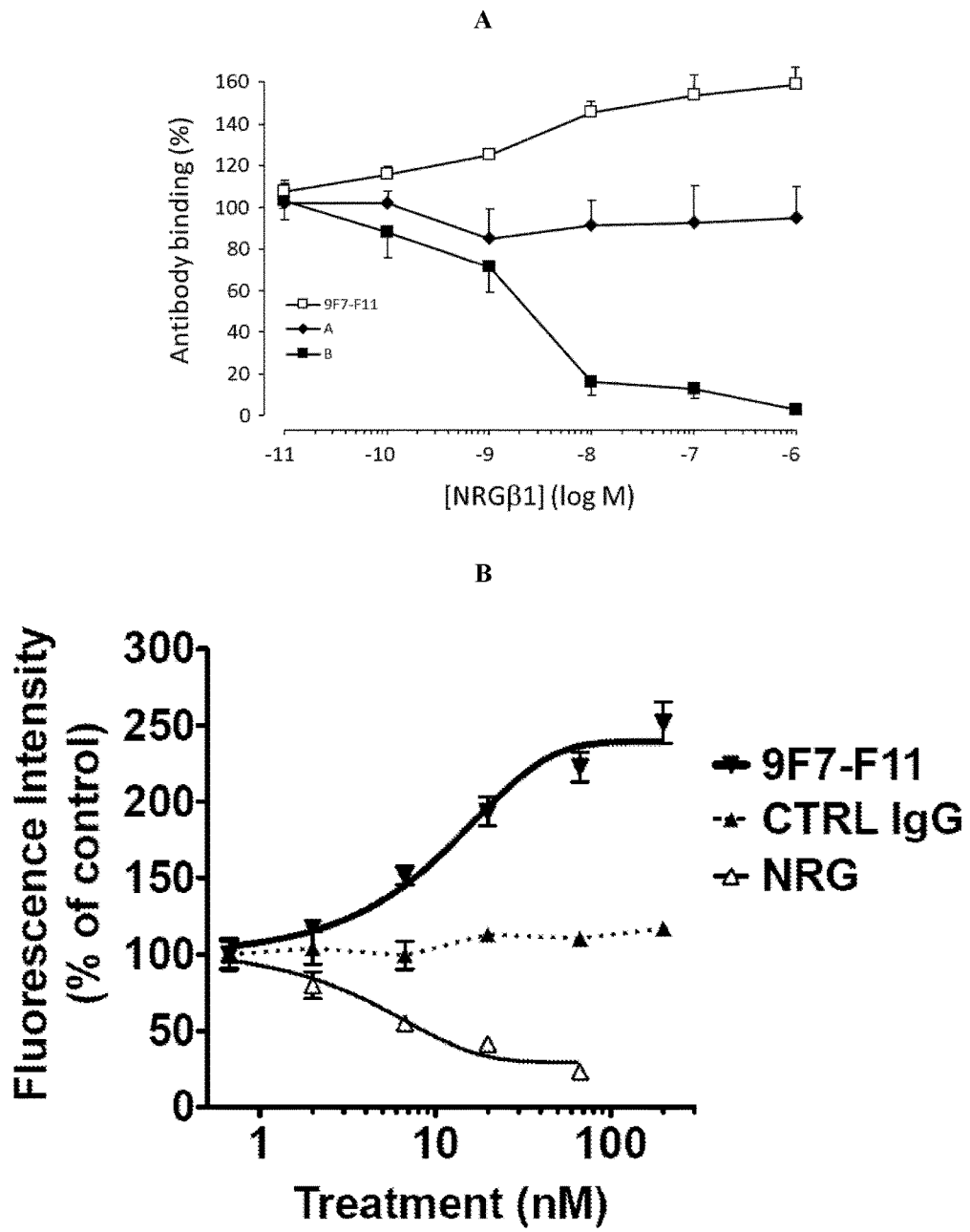

Cytometry competition experiment was performed in order to quantify the ability of NRG to inhibit antibody binding to HER3 in a SKBR3 cell-based assay. To this end, 10$^5$ SKBR3 cells were pre-incubated with various concentrations of the competing NRG ligand for 1.5 h on ice. After one washing with PBS-1% BSA, selected anti-HER3 mAb 9F7-F11, at concentration giving 50% maximal binding, was added to each well for 1 h on ice. In some experiments, NRG ligand and anti-HER3 9F7-F11 were co-incubated for 2 h on ice. Cells were then washed and further incubated with a 1:60 dilution of appropriate FITC-conjugated secondary antibody (Sigma) for 45 min on ice, before cytometry analysis on a Quanta apparatus (Beckman-Coulter). Competition experiments by FACS demonstrated that 9F7-F11 antibody did not compete with NRG, thus suggesting that this antibody did not bind to the NRG-binding site (FIG. 1A). NRG-non competitive 9F7-F11 antibody binding was even enhanced to 160% when NRG was added, thus demonstrating an allosteric effect of mAb 9F7-F11 for HER3 binding. In contrast, binding of the positive control antibody A was not modified by NRG incubation, and positive-control antibody B showed a NRG-dependent binding (FIG. 1A).

Figure 7:
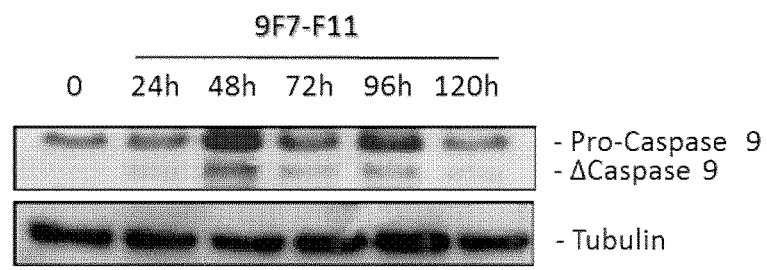
FIG. 7 shows the effects of mAb 9F7-F11 on apoptosis of BxPC3 pancreatic cancer cells (A). The cleavage of caspase-9, which initiates mitochondrial apoptosis, is demonstrated by western blot of cell lysates from 9F7-F11-treated BxPC3 cells (B).

Inversely, 10$^5$ HER3-transfected 3T3 fibroblasts were cultured during 2 days before starvation, and then incubated with various concentrations of 9F7-F11 mAb in KREBS buffer for 45 minutes at +4° C. NRG labelled with d2 cryptate dye was added for additional 45 minutes. After KREBS washing, fluorescence at 620/670 nm was measured using a Pherastar microplate reader. As demonstrated in FIG. 1B, 9F7-F11 binding induced an increase of NRG binding to HER3 whereas irrelevant IgG did not. As control, various concentrations of free NRG displaced binding of labelled NRG to the HER3 receptor (FIG. 1B), thus demonstrating a mutual allosteric effect between 9F7-F11 and NRG for HER3 binding.

EXAMPLE 2: NRG ADDITION INDUCES A 6-FOLD INCREASE OF 9F7-F11 AFFINITY TO THE HER3 RECEPTOR

Figure 2:
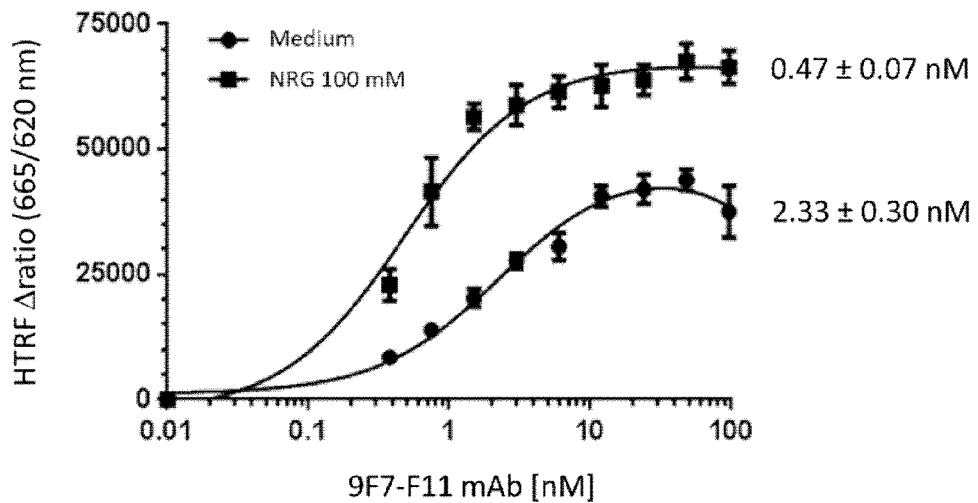

Using the Tag-Lite technology developed by CisBio BioAssay, 10$^4$ HER3 Snap-tagged HEK cells were labelled with Lumi4-terbium cryptate donor, and then co-incubated with NRG and various concentrations of d2 acceptor-labelled mAb 9F7-F11. After 16 h of incubation, the fluorescence of Lumi4-terbium and d2 was measured respectively at 620 and 665 nm (60 µs delay, 400 µs integration) upon 337 nm excitation on a Pherastar FS instrument. As demonstrated in FIG. 2, a dose-dependent increase of 9F7-F11 binding to the HER3 receptor was observed in the presence of NRG, with regard to lower HER3 binding measured without NRG. The $K_d$ value of 9F7-F11 binding to HER3 was calculated to 0.47±0.07 nM following co-incubation with NRG whereas $K_d$ was measured at 2.33±0.30 nm without NRG; thus demonstrating that NRG addition allosterically induces a 6-fold increase of 9F7-F11 affinity to the HER3 receptor.

EXAMPLE 3: ANTI-HER3 NRG-NON COMPETITIVE ALLOSTERIC ANTIBODY 9F7-F11 INHIBITS HER2 AND HER3 PHOSPHORYLATION, TOGETHER WITH THE BLOCKADE OF ERK1/2 AND AKT PHOSPHORYLATION

Five hundred and thousand pancreatic BxPC3 tumor cells were added to each well of a 6-well culture plate for 24 h at 37° C. After serum starvation for 16 h in a RPMI complete medium with 1% FCS and further washing, cells were pre-incubated with a 50 µg/ml concentration of antibody 9F7-F11, or negative control antibody for 15 minutes or 1 h at 37° C., before washing and subsequent stimulating or not with a 100 ng/ml dilution of NRG. Cells were then washed, scraped and lysed with buffer containing 20 mM Tris-HCl pH 7.5, 150 mM NaCl, 1.5 mM $MgCl_2$, 1 mM EDTA, 1% Triton, 10% glycerol, 0.1 mM Phenylmethylsulfonyl fluoride, 100 mM sodium fluoride, 1 mM sodium orthovanadate (Sigma-Aldrich), and one complete protease inhibitor mixture tablet (Roche Diagnostics, Indianapolis, Ind.). After a 30 min-incubation time, samples were cleared of insoluble fraction by centrifugation and protein concentrations in cell lysates were determined by Bradford assay. These protein lysates were directly mixed with Laemmli buffer (1-20 µg total proteins depending on the target and cell lines) and heated at 95° C. for 5 minutes. After electrophoresis on 7% SDS-PAGE under reducing conditions, the proteins were transferred to polyvinylidene difluoride membranes (Millipore) which were then saturated in TNT buffer (Tris 25 mM pH 7.4, NaCl 150 mM, Tween 0.1%) containing 5% nonfat dry milk for 1 h at 25° C. Primary antibodies, directed to kinase receptors or signaling kinases, and their phosphorylated forms, were incubated in TNT-5% BSA buffer for 18 h at 4° C. After five washes in TNT buffer, peroxidase-conjugated rabbit, goat or mouse polyclonal antibodies (Sigma-Aldrich) were added as appropriate in TNT buffer containing 5% nonfat dry milk for 1 h at 25° C. After five washes in TNT buffer, the blots were visualized using a chemiluminescent substrate (Western lightning Plus-ECL, Perkin Elmer).

Figure 3:
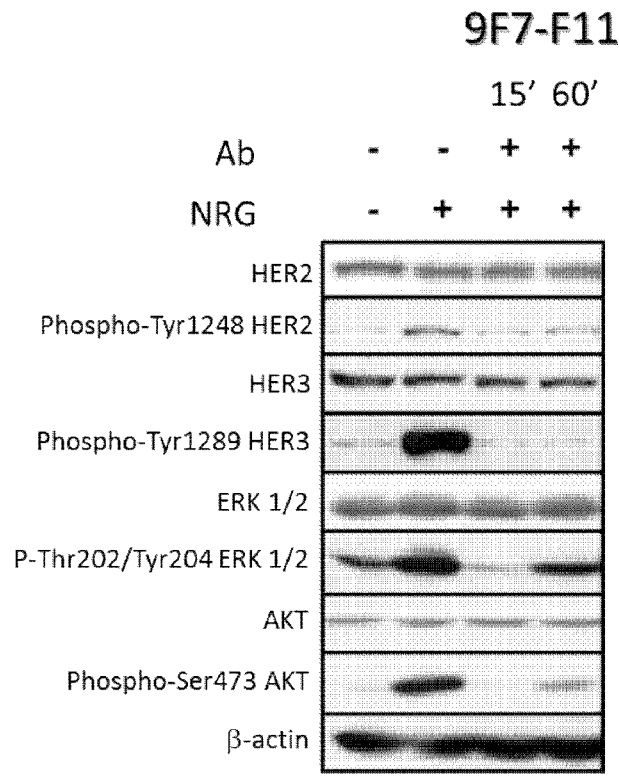
FIG. 3 shows the inhibition of phosphorylation of HER2/HER3 receptors and dowstream PI3K/Akt and ERK signalling by using anti-HER3 mAb 9F7-F11 in BxPC3 pancreatic carcinoma cells.

Remarkably, 9F7-F11 antibody blocked ligand-induced phosphorylation on Y1289-HER3 and Y1242-HER2 (FIG. 3). Concomitantly, allosteric non-competitive antibody 9F7-F11 induced inhibition of Akt phosphorylation on Ser473, and ERK1/2 phosphorylation on Thr202/204.

EXAMPLE 4: ANTI-HER3 NRG-NON COMPETITIVE ALLOSTERIC ANTIBODY 9F7-F11 INHIBITS MDM2 EXPRESSION AND PHOSPHORYLATION, TOGETHER WITH THE MODULATION OF THE P53 PATHWAY

Figure 4:
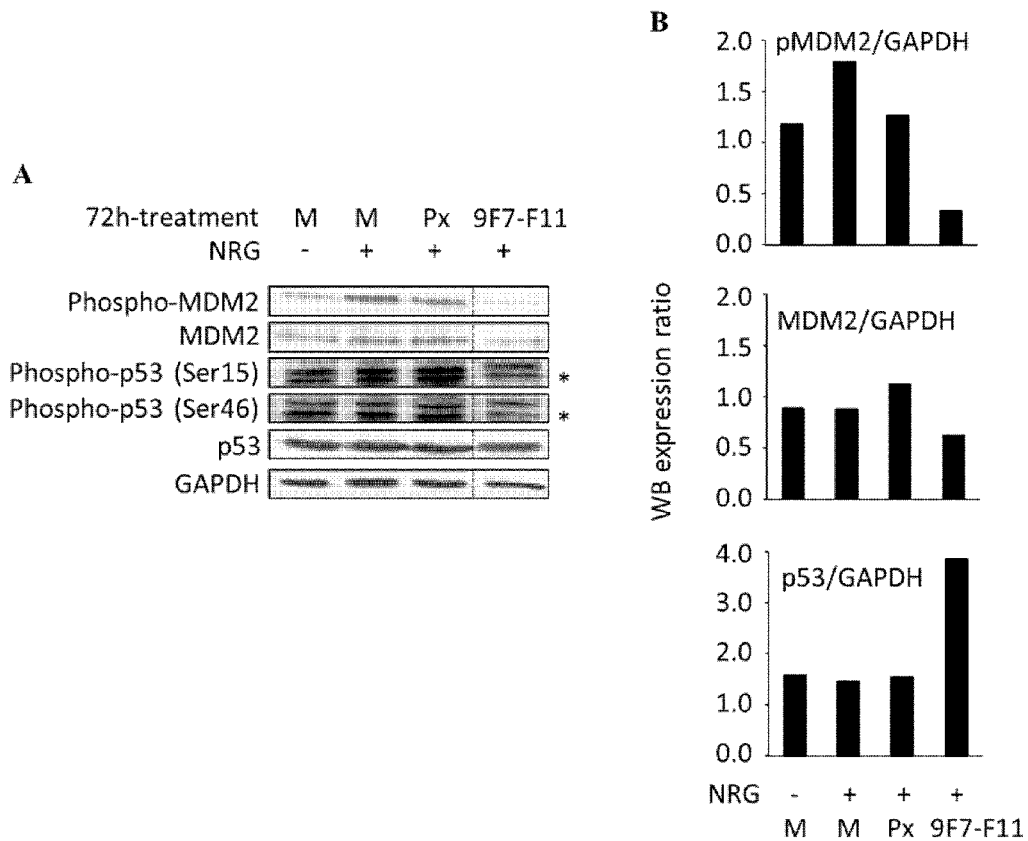
FIG. 4 shows the effects of mAb 9F7-F11 on p53/MDM2 expression and phosphorylation, as demonstrated by western blot (A) and quantified by Image J (B).
Figure 5:
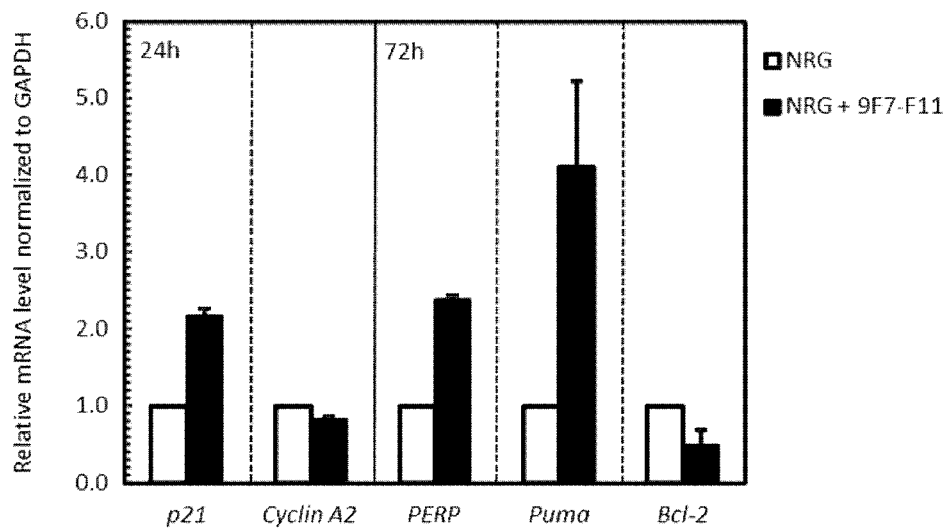
FIG. 5 shows the effects of mAb 9F7-F11 on the expression of p53-inducible genes p21, Cyclin A2, PERP, Puma and Bcl-2, as demonstrated by quantitative PCR. Relative mRNA expression was normalized with regard to GAPDH expression.

Similarly as described above, BxPC3 tumor cells were added to each well of a 6-well culture plate for 24 h at 37° C. After serum starvation for 16 h in a RPMI complete medium with 1% FCS and further washing, cells were pre-incubated with a 50 µg/ml concentration of antibody 9F7-F11, or negative control antibody for 24 h or 72 h at 37° C., before washing and subsequent stimulation or not with a 100 ng/ml dilution of NRG. Cells were subsequently lysed for SDS-PAGE and western blot, or were submitted to RNA extraction, reverse transcription and quantitative PCR using appropriate primers. As demonstrated in FIG. 4 by western blot, 9F7-F11 treatment inhibited MDM2 expression and phosphorylation, and increased p53 expression. In correlation, 9F7-F11 treatment increased p53-inducible gene expression such as p21, which is implicated in the blockade of cell cycle and proliferation, and Puma and PERP, which positively-regulated apoptosis, as demonstrated by Q-PCR (FIG. 5). In contrast Cyclin A2 and Bcl2 gene expression, which promotes proliferation and inhibits apoptosis, respectively, were reduced following treatment with NRG-non competitive allosteric antibody 9F7-F11 (FIG. 5).

EXAMPLE 5: ANTI-HER3 NRG-NON COMPETITIVE ALLOSTERIC ANTIBODY 9F7-F11 BLOCKS CELL CYCLE IN G1 PHASE, INHIBITS PROLIFERATION AND RESTORES APOPTOSIS

Figure 6:
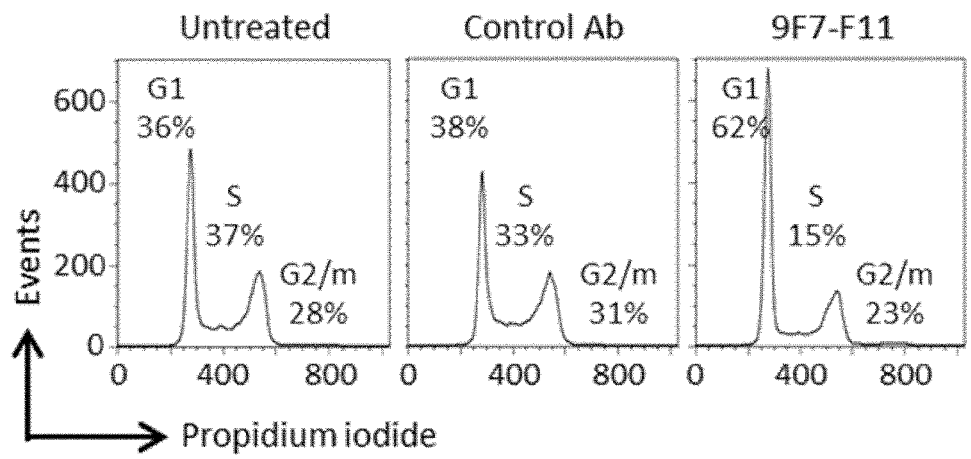
FIG. 6 shows the effects of mAb 9F7-F11 on cell cycle arrest of BxPC3 pancreatic cancer cells.
Figure 8:
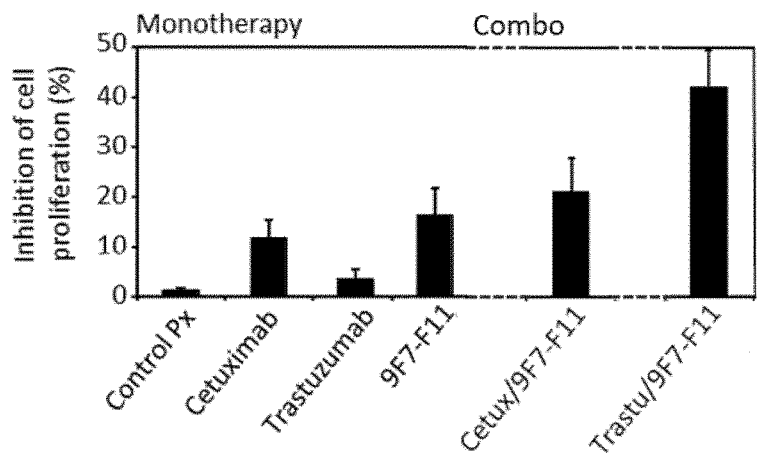
FIG. 8 shows the effects of mAb 9F7-F11, alone or in combination with cetuximab or trastuzumab, on proliferation of BxPC3 pancreatic cancer cells, with regard to the effects observed with trastuzumab or cetuximab alone.

The effect of HER3-specific Ab 9F7-F11 on the cell cycle was evaluated using propidium iodide staining. Briefly, 300,000 BxPC3 tumor cells/well were cultured in 6-well microtiter plates for 24 h, and then serum starved and synchronized in RPMI medium without FCS for another 24 h, before co-incubation with 100 µg/ml anti-HER3 Ab 9F7-F11 and 100 ng/ml NRG. Permeabilized cells were stained 24 h later with propidium iodide before flow cytometric analysis. For proliferation and apoptosis assays, 50,000 BxPC3 cells/well were plated one day before starvation (in RPMI-1% FCS). HER3-specific Ab 9F7-F11 and NRG were then added for 120 h. Cell proliferation was measured by incorporating Alexa Fluor 488-conjugated 5-ethynyl-2'-deoxyuridine (EdU) (Invitrogen) during the last 30 h of culture. Cell apoptosis was assessed by incubation with fluorescence-conjugated Annexin V and 7-aminoactinomycin D (7-AAD; Beckman-Coulter). All experiments were performed in triplicate. For caspase-9 analysis, BxPC3 cells were treated and lysed as described above. Following SDS-PAGE and western blot of cell lysates, activation of capase-9 through cleavage of the pro-enzyme was evidenced using appropriate antibody. As indicated in FIG. 6, 24 h-treatment of allosteric 9F7-F11 Ab blocked cell cycle in G1 phase, with a G1 cell increase from 36-38% for untreated or control Ab-treated cells to 62% for 9F7-F11-treated BxPC3 cells. 9F7-F11 treatment concomitantly reduced the percentage of BxPC3 cells in S and G2/m phase (FIG. 6). Treatment of BxPC3 cells with 9F7-F11 mAb increased early (18%) and late (12%) apoptosis, in comparison to untreated and control Ab-treated cells (FIG. 7A), with concomitant cleavage of pro-caspase-9, which initiates mitochondrial apoptosis (FIG. 7B). Finally, BxPC3 cell proliferation was inhibited following 120 h-treatment with 9F7-F11 Ab. No specific effect on cell proliferation was observed with anti-HER2 trastuzumab alone on $HER2^{low}$ BxPC3 cells whereas anti-EGFR cetuximab was less efficient than anti-HER3 Ab 9F7-F11 (FIG. 8). In contrast, combination of mAb 9F7-F11 and trastuzumab was more efficient to inhibit cell proliferation than 9F7-F11/cetuximab combo, suggesting a possible synergistic effect of trastuzumab/9F7-F11 combo vs an additive effect of cetuximab/9F7-F11 combo on $HER2^{low}$ tumor cells. Taken together, these results demonstrated that NRG-non competitive allosteric anti-HER3 antibody 9F7-F11 blocks cell cycle in G1 phase, restores early and late mitochondrial apoptosis through pro-capase-9 cleavage and inhibits proliferation of tumor cells. In this case, combination of mAb 9F7-F11 with anti-HER2 Abs could be of great interest in HER2$^{low}$ tumors.

EXAMPLE 6: ANTI-HER3 NRG-NON COMPETITIVE ALLOSTERIC ANTIBODY 9F7-F11 INDUCES ANTIBODY-DEPENDENT CELL CYTOTOXICITY OF BREAST CANCER CELLS

Figure 9:
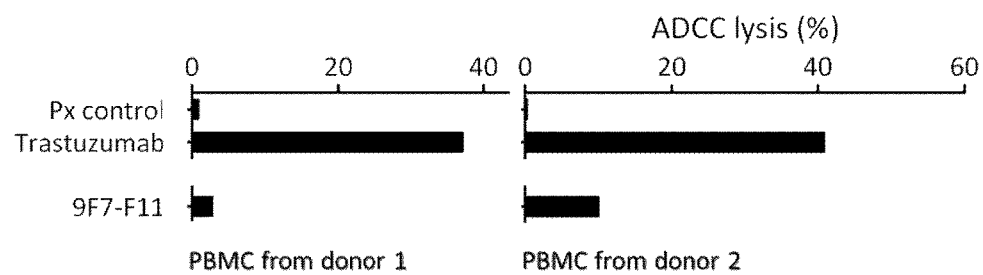
FIG. 9 shows the ADCC effect of mAb 9F7-F11 vs trastuzumab on target MDA-MB-453 breast cancer cells.

MDA-MB-453 tumor target cells, derived from a basal-like triple-negative breast cancer, were plated at 20,000 cells/well of flat-bottom 96-well microplate one day before ADCC assay. MDA-MB-453 cell line expresses around 180,000 HER2 and 21,000 HER3 receptors whereas no EGFR expression is observed. After washing in culture medium, 9F7-F11 mAb was added at 10 µg/ml during 30 minutes, before addition of effector cells derived from peripheral mononuclear cells (PBMC). PBMC were prepared by density gradient centrifugation of blood samples from healthy donors obtained at the "Etablissement Français du Sang". Effector/Target (E/T) cells were incubated at a 15/1 E/T ratio for 24 h in a humidified cell incubator. The killing of MDA-MB-453 target cells was assessed by measuring Lactate Dehydrogenase (LDH) release from damaged cells using the Cytotoxicity Detection kit (LDH Detection kit; Promega G-1780) according to the manufacturer's instruction. Briefly 50 µl of cell supernatant was carefully transferred to new flat-bottom 96-well microplate, and LDH reaction mixture (50 µl/well) from the kit was added to each well. After 30 min incubation at 37° C., 50 µl of stop solution (available in the kit) was added and the optical density was measured at 490 nm. The following controls were set up for each experiment: PBMC alone, MDA-MB-453 target cells alone (spontaneous LDH release), target cells with PBMC (antibody dependent spontaneous release), target cells with lysis buffer (maximum LDH release), PBMC with Ab, target cells with Ab. The percent specific lysis of each sample was determined using the following formula: percent specific lysis=(sample value−spontaneous release)/(maximum release−spontaneous release)*100. As shown in FIG. 9, 9F7-F11 Ab induced a 5 to 10% specific cell lysis of MDA-MB-453 breast cancer cells using PBMC from healthy donors 1 and 2. In the same experiment, positive control trastuzumab induced around 40% lysis, due to the fact that MDA-MB-453 express ten-fold more HER2 receptors than HER3 receptors.

EXAMPLE 7: 9F7-F11 MONOTHERAPY IN MICE XENOGRAFTED WITH HER2-AMPLIFIED MDA-MB-361 AND TRIPLE-NEGATIVE MDA-MB-468 BREAST CANCERS

Athymic, 6- to 8-week-old, female BALB/c nude mice were purchased from Janvier and Charles Rivers Laboratories. HER2-amplified/PIK3CA-mut breast cancer cells MDA-MB-361 (10×10$^6$) and HER2-non amplified/PTEN-mut/p53-mut/ER-/PR-triple-negative breast cancer cells MDA-MB-468 (3.5×10$^6$) were injected s.c. into the right flank of athymic BALB/c nude mice. They both expressed HER3 receptor at low level (around 10,000 receptors/cell). All in vivo experiments were done in compliance with the French guidelines for experimental animal studies (Agreement no. B34-172-27).

Tumor-bearing mice were randomized in the different treatment groups when the tumors reached an approximate volume of 100 mm$^3$. The mice were treated by i.p. injections of HER3-specific antibodies 9F7-F11 vs vehicle (PBS). The amount of injected antibody was 300 µg/injection (15 mg/kg), thrice a week, for 6 weeks consecutively (Q2D-6W). Tumor dimensions were measured twice weekly with a caliper and the volumes were calculated by the formula D1×D2×D3/2. Tumor progression was calculated using the formula [(final volume)−(initial volume)]/(initial volume). The results were also expressed by a Kaplan-Meier survival curve, using the time taken for the tumor to reach a determined final volume of 2,000 mm$^3$. A median delay was defined as the time at which 50% of the mice had a tumor reaching the determined volume.

Figure 10:
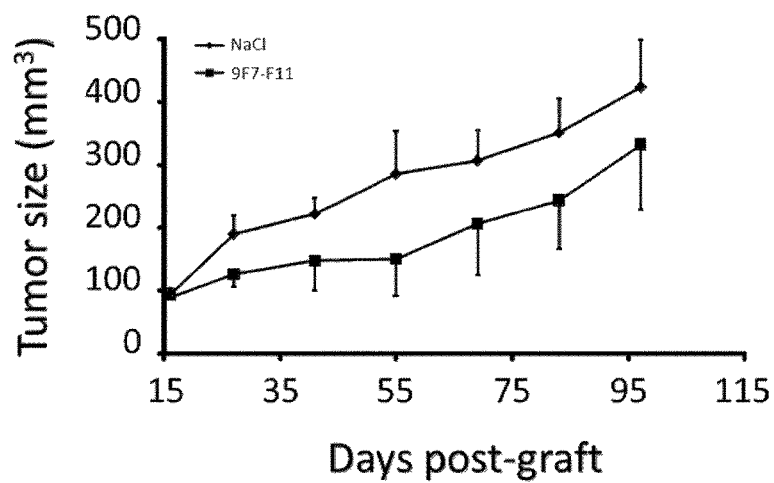
FIG. 10 shows the inhibition of tumor progression by mAb 9F7-F11 in nude mice xenografted with HER2-amplified/PIK3CA-mut MDA-MB-361 breast cancer cells.

As shown in FIG. 10, we observed a significant 47±5%-reduction in MDA-MB-361 tumor growth in 9F7-F11-treated mice at day 55 post-tumor implantation (corresponding to the end of antibody treatment; day 40), with regard to mean tumor size measured in mice treated with vehicle (p<0.001). At the end of the experiment (97 days), a smaller, but significant, 21±2%-reduction in tumor size was observed in 9F7-F11-treated group, probably because 9F7-F11 treatment was stopped since 57 days.

Figure 11:
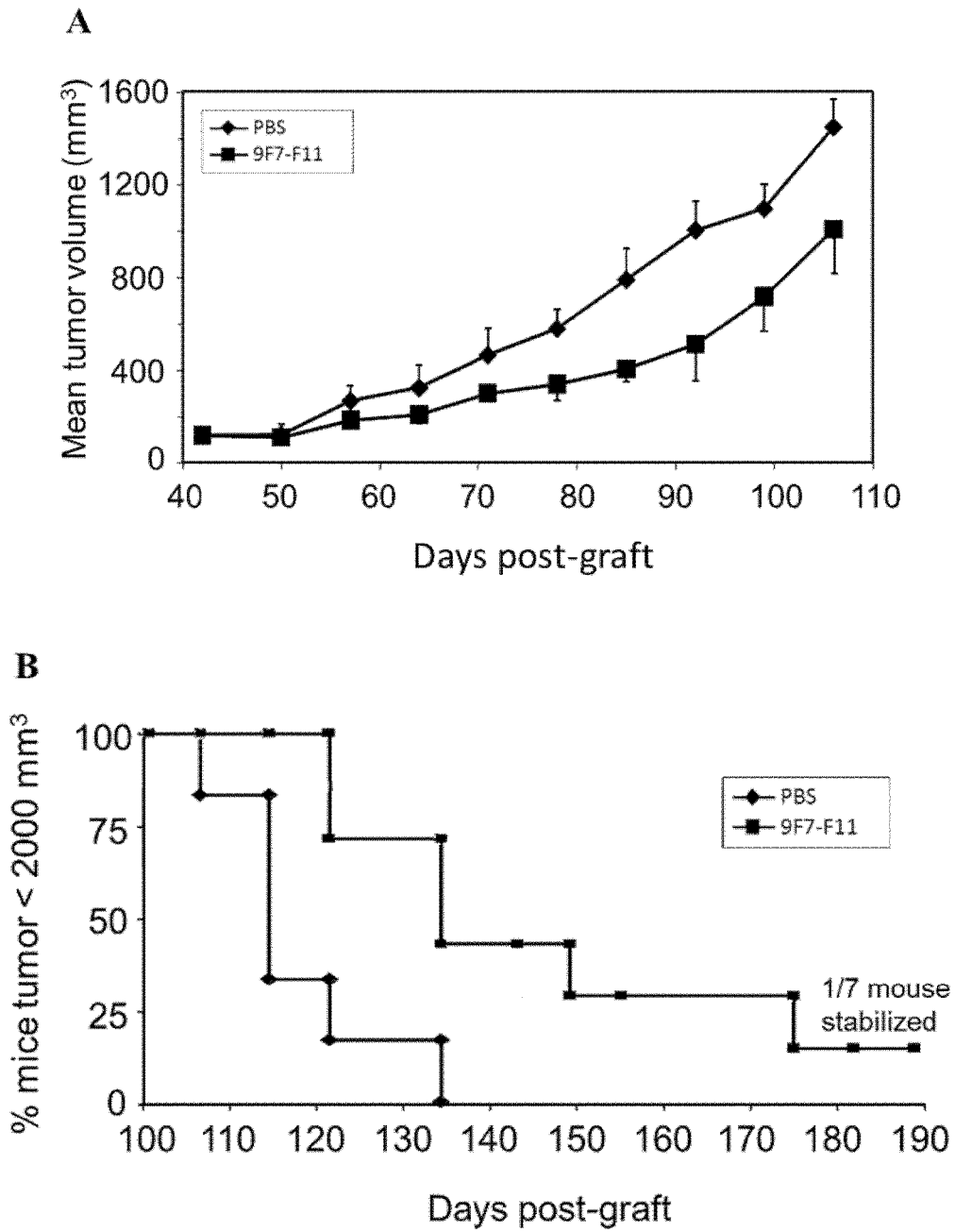
FIG. 11 shows the inhibition of tumor progression by mAb 9F7-F11 in nude mice xenografted with triple-negative PTEN-mut/p53-mut MDA-MB-468 breast cancer cells (A). Kaplan-Meier survival curve was calculated when MDA-MB-468 tumors reached a volume of 2000 mm$^3$ (B).

A shown in FIG. 11A, mean tumor volume was significantly lower in 9F7-F11-treated mice xenografted with MDA-MB-468 cells (35% volume reduction at day 105 post-xenograft following treatment with 9F7-F11) than in controls (vehicle). Treatment with the 9F7-F11 Ab significantly delayed the 50% median survival time by 20 days in animals xenografted with MDA-MB-468 cells (one mouse was stabilized for the 9F7-F11-treated group at the end of the experiment, i.e., 190 days; p<0.05). Taken together, these results demonstrate that NRG-non competitive allosteric anti-HER3 Ab 9F7-F11 delayed tumor growth in mice xenografted with either HER2-amplified or triple-negative breast cancer cell lines.

EXAMPLE 8: 9F7-F11 COMBOTHERAPY WITH PERTUZUMAB IN MICE XENOGRAFTED WITH NRG-ADDICTED BXPC3 PANCREATIC CANCER

We previously demonstrated that combination of therapeutic antibody trastuzumab with other targeted therapies demonstrated a synergistic effect on pancreatic carcinomas with low HER2 expression (Larbouret, 2007, 2010). We now assessed a combotherapy with allosteric anti-HER3 Ab 9F7-F11 and anti-HER2 Ab Pertuzumab in HER2$^{low}$ pancreatic carcinoma. Six week/old female athymic mice were injected subcutaneously into the right flank with HER2$^{low}$ pancreatic BxPC-3 cells (4.5×10$^6$) which secreted neuregulin (NRG-addicted). Tumor-bearing mice were randomized to different treatment groups (at least 6 animals/group) when tumors reached a volume of 100 mm$^3$ and were then treated with 2 or 10 mg/kg pertuzumab, 10 mg/kg 9F7-F11 or the pertuzumab plus 9F7-F11 combination (10 mg/kg of each mAb). Antibodies were given intraperitonally (i.p.) twice a week for 4 weeks (Q3D-4W). Tumor volumes were calculated by the formula: $D_1 \times D_2 \times D_3/2$. For survival comparison, mice were sacrificed when tumor reached a volume of 1000 mm$^3$.

Figure 12:
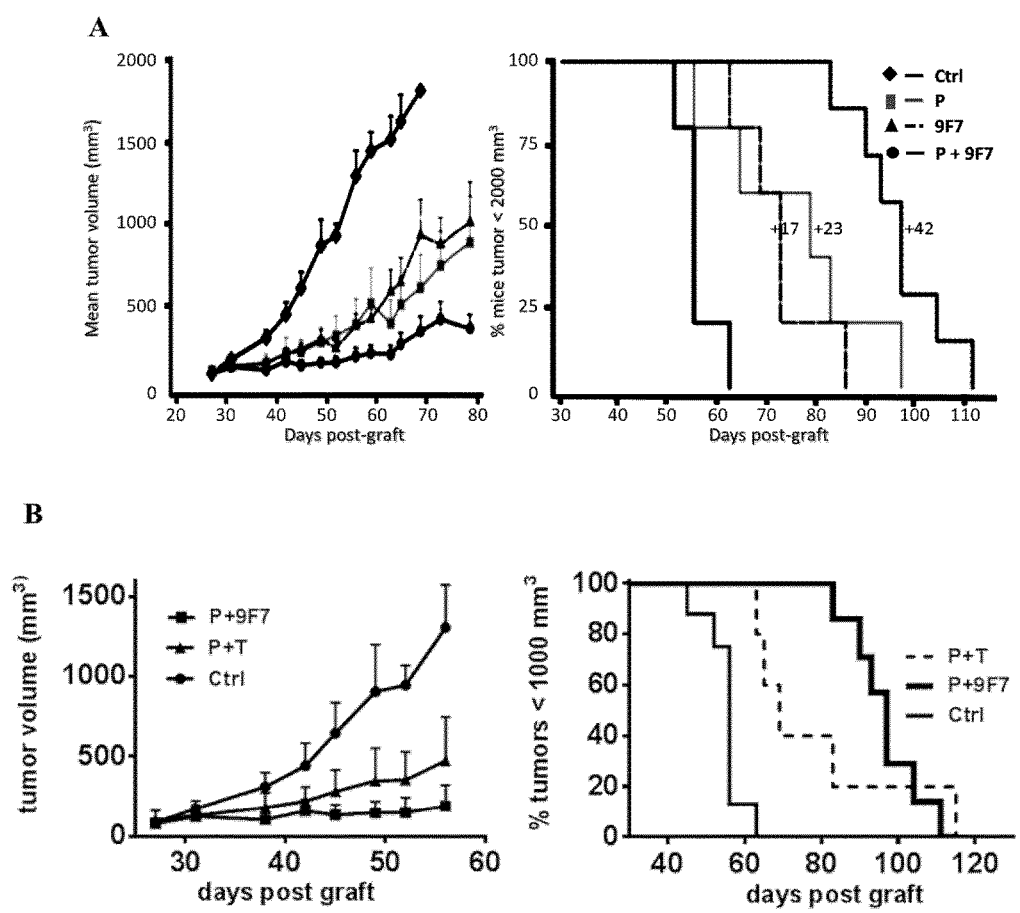
FIG. 12 shows the tumor progression and survival of nude mice xenografted with NRG-addicted, p53-mut, HER2$^{low}$ BxPC3 pancreatic cancer cells and treated with mAb 9F7-F11, used alone (9F7) or in combination with pertuzumab (P+9F7), with comparison to pertuzumab alone (P) or vehicle (Ctrl) (Panel A) and the combination of trastuzumab and pertuzumab (P+T) (Panel B).

Both antibodies alone markedly slowed down tumor growth compared with the untreated group (p<0.001) and no significant difference was observed between anti-HER3 Ab 9F7-F11 and pertuzumab (p=0.6488) (FIG. 12A). The 50% median survival time was significantly delayed by 17 days in mice treated with 9F7-F11 and by 23 days in mice treated with pertuzumab in comparison to controls (FIG. 12A).

Moreover, co-treatment with 9F7-F11 and pertuzumab inhibited tumor growth much more than each antibody alone (pertuzumab versus 9F7-F11/pertuzumab; p=0.004). At the end of the 4-week treatment, tumor volume kept increasing in mice treated with 9F7-F11 or pertuzumab alone, whereas it remained quite stable in animals that received the 9F7-F11/pertuzumab combination (FIG. 12A). Median survival was longer in animals treated with the two-antibody combination than in control animals (gain of 42 days; p=0.0001) or mice that received a single antibody (9F7-F11/pertuzumab vs 9F7-F11 p=0.0013; 9F7-F11/pertuzumab vs pertuzumab p=0.0355) (FIG. 12A). Finally the combination of anti-HER3 Ab 9F7-F11 and pertuzumab was markedly more efficient than pertuzumab/trastuzumab combo, with mean survival time longer in animals treated with 9F7-F11/pertuzumab (42 days) than in animal treated with pertuzumab/trastuzumab (13 days) (FIG. 12B). Taken together, these results demonstrated that combotherapy using NRG-non competitive allosteric anti-HER3 Ab 9F7-F11 and anti-HER2 pertuzumab is more efficient in HER2$^{low}$ tumors than combotherapy using two HER2-specific antibodies.

EXAMPLE 9: HER3 KNOCK-OUT ABROGATES 9F7-F11 IN VIVO EFFICIENCY IN MICE XENOGRAFTED WITH NRG-ADDICTED BXPC3 PANCREATIC CANCER

Based on the work of Lee-Hoeflich et al. (2008), two short hairpin oligonucleotides were chosen to knockdown HER3 mRNA levels at described in supporting materials and methods. The control vector (shCTRL) pSIREN-shLuc was kindly provided by L. Le Cam and described previously (Le Cam et al., 2006). pSIREN-shHER3 and pSIREN-shLuc, which contain the puromycin N-acetyl transferase resistance gene, were then transfected in the amphotropic packaging cell line AmphoPack-293 (Clontech). After 2 days, supernatants containing replication-defective virus particles were collected and used to infect BxPC3 cells. Antibiotic selection (10 μg/ml puromycin) was started two days later. After 7 days of selection, cells were subcloned and selected based on the absence of endogenous HER3 protein expression. Six week/old female athymic mice, purchased from Harlan (Le Malcourlet, France), were injected subcutaneously into the right flank with parental shHER3 ($3.5 \times 10^6$), or control shLuc BxPC-3 cells ($4.5 \times 10^6$) as describe above. Tumor-bearing mice were randomized to different treatment groups (at least 6 animals/group) when tumors reached a volume of 100 mm$^3$ and were then intraperitoneally-treated with 10 mg/kg 9F7-F11 twice a week for 4 weeks (Q3D-4W).

Figure 13:
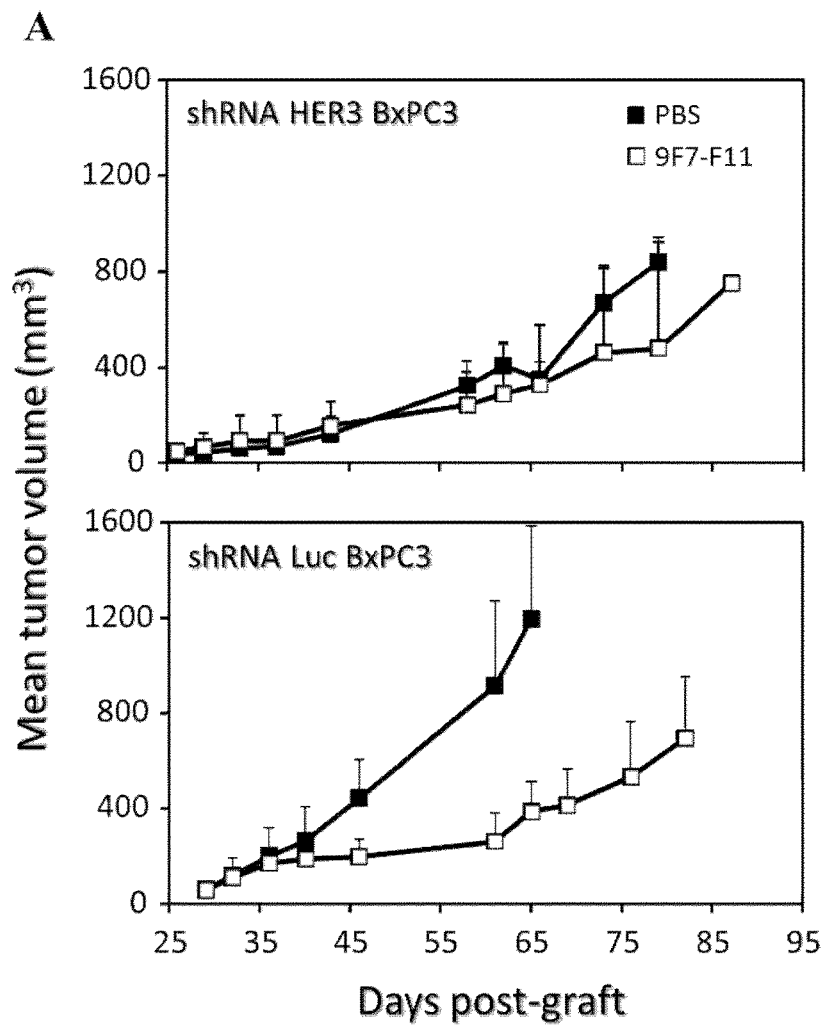
FIG. 13 shows the inhibition of tumor progression by mAb 9F7-F11 in nude mice xenografted with shHER3- or shLuc (control)-knock out BxPC3 pancreatic cancer cells (A). HER3 silencing is checked by western blot on xenografts recovered from treated mice (B).
Figure 13:
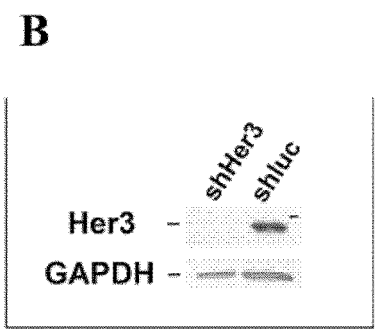

To confirm the relationship between HER3 expression and 9F7-F11 therapeutic efficacy in vivo, mice were xenografted with shHER3 or shCTRL BxPC-3 cells (FIG. 13A). In agreement with our in vitro data, NRG-non competitive allosteric anti-HER3 antibody 9F7-F11 significantly inhibited the growth of shCTRL BxPC-3 tumor xenografts in comparison to untreated controls (p<0.0001 and p=0.0015) (FIG. 13A). In contrast, no significant tumor growth regression was observed in mice xenografted with shHER3 BxPC-3 cancer cells and treated with 9F7-F11 Ab in comparison to untreated controls (FIG. 13A). At the end of the experiment, HER3 expression was still silenced in shHER3 BxPC-3 tumor xenografts isolated from treated mice (FIG. 13B). These results indicate that HER3 knockdown in vivo abrogates therapeutic efficacy of NRG-non competitive allosteric anti-HER3 antibody 9F7-F11.

REFERENCES

Throughout this application, various references describe the state of the art to which this invention pertains. The disclosures of these references are hereby incorporated by reference into the present disclosure.

The invention claimed is:

1. An neuregulin noncompetitive allosteric anti-human-HER3 antibody comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

2. The antibody of claim 1 wherein the heavy chain variable region of said antibody has the amino acid sequence set forth as SEQ ID NO: 1 and/or the light chain variable region has the amino acid sequence set forth as SEQ ID NO: 5.

3. The antibody of claim 1 which is a chimeric antibody.

4. The antibody of claim 3 wherein the chimeric antibody is a chimeric mouse/human antibody.

5. The antibody of claim 1 which is a humanized antibody.

6. A fragment of an antibody according to claim 1, wherein said fragment is selected from the group consisting of Fv, Fab, F(ab')2, Fab', dsFv, scFv, sc(Fv)2 and diabodies.

7. A nucleic acid sequence encoding i) a neuregulin noncompetitive allosteric anti-human-HER3 antibody comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region, or ii) a fragment of the neuregulin noncompetitive allosteric anti-human-HER3 antibody, wherein said fragment is selected from the group consisting of Fv, Fab, F(ab')2, Fab', dsFv, scFv, sc(Fv)2 and diabodies.

8. The nucleic acid sequence of claim 7, wherein the neuregulin noncompetitive allosteric anti-human-HER3 antibody is a monoclonal antibody.

9. The nucleic acid sequence of claim 8 which is SEQ ID NO:9 or SEQ ID NO:10.

10. A vector comprising a nucleic acid encoding
i) a neuregulin noncompetitive allosteric anti-human-HER3 antibody comprising an heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region, or ii) a fragment of the neuregulin noncompetitive allosteric anti-human-HER3 antibody, wherein said fragment is selected from the group consisting of Fv, Fab, F(ab')2, Fab', dsFv, scFv, sc(Fv)2 and diabodies, wherein the neuregulin noncompetitive allosteric anti-human-HER3 antibody is a monoclonal antibody.

11. A host cell comprising
a. a nucleic acid encoding
i) a neuregulin noncompetitive allosteric anti-human-HER3 antibody comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region, or ii) a fragment of the neuregulin noncompetitive allosteric anti-human-HER3 antibody, wherein said fragment is selected from the group consisting of Fv, Fab, F(ab')2, Fab', dsFv, scFv, sc(Fv)2 and diabodies, wherein the neuregulin noncompetitive allosteric anti-human-HER3 antibody is a monoclonal antibody;

or b. a vector comprising the nucleic acid.

12. A pharmaceutical composition comprising
i) a neuregulin noncompetitive allosteric anti-human-HER3 antibody comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region, or ii) a fragment of the neuregulin noncompetitive allosteric anti-human-HER3 antibody, wherein said fragment is selected from the group consisting of Fv, Fab, F(ab')2, Fab', dsFv, scFv, sc(Fv)2 and diabodies.

13. A method for treating cancer in a subject in need thereof comprising administering to the subject a therapeutically effective amount of
i) a neuregulin noncompetitive allosteric anti-human-HER3 antibody comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region, or ii) a fragment of the neuregulin noncompetitive allosteric anti-human-HER3 antibody, wherein said fragment is selected from the group consisting of Fv, Fab, F(ab')2, Fab', dsFv, scFv, sc(Fv)2 and diabodies.

14. A method of diagnosing cancer, comprising
contacting a biological sample of a subject with or likely to suffer from a cancer associated with HER3 expression with
i) a neuregulin noncompetitive allosteric anti-human-HER3 antibody comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region, or ii) a fragment of the neuregulin noncompetitive allosteric anti-human-HER3 antibody, wherein said fragment is selected from the group consisting of Fv, Fab, F(ab')2, Fab', dsFv, scFv, sc(Fv)2 and diabodies, wherein said step of contacting is performed under conditions sufficient for the neuregulin noncompetitive allosteric anti-human-HER3 antibody or the fragment of the neuregulin noncompetitive allosteric anti-human-HER3 antibody to form complexes with cells of the biological sample that express HER3; and detecting and/or quantifying said complexes, whereby detection of said complexes is indicative of the presence of a cancer associated with HER3 expression in said subject.

* * * * *

SEQUENCE LISTING

<160> NUMBER OF SEQ ID NOS: 10

<210> SEQ ID NO 1
<211> LENGTH: 117
<212> TYPE: PRT
<213> ORGANISM: Mus musculus

<400> SEQUENCE: 1

```
Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Asp Gly Gly Val Thr Tyr Tyr Pro Asp Thr Ile
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Tyr Gly Leu Phe Ala Tyr Trp Gly Gln Gly Thr Leu
            100                 105                 110

Val Thr Val Ser Ala
        115
```

```
<210> SEQ ID NO 2
<211> LENGTH: 8
<212> TYPE: PRT
<213> ORGANISM: Mus musculus

<400> SEQUENCE: 2

Gly Phe Thr Phe Ser Ser Tyr Thr
1               5

<210> SEQ ID NO 3
<211> LENGTH: 8
<212> TYPE: PRT
<213> ORGANISM: Mus musculus

<400> SEQUENCE: 3

Ile Ser Asp Gly Gly Gly Val Thr
1               5

<210> SEQ ID NO 4
<211> LENGTH: 10
<212> TYPE: PRT
<213> ORGANISM: Mus musculus

<400> SEQUENCE: 4

Ala Arg Asp Arg Tyr Gly Leu Phe Ala Tyr
1               5                   10

<210> SEQ ID NO 5
<211> LENGTH: 107
<212> TYPE: PRT
<213> ORGANISM: Mus musculus

<400> SEQUENCE: 5

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Ile Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Asn Tyr Pro Tyr
                85                  90                  95

Thr Phe Gly Gly Gly Thr Lys Leu Glu Ile Lys
            100                 105

<210> SEQ ID NO 6
<211> LENGTH: 6
<212> TYPE: PRT
<213> ORGANISM: Mus musculus

<400> SEQUENCE: 6

Gln Asn Val Gly Ile Ala
1               5

<210> SEQ ID NO 7
<211> LENGTH: 3
<212> TYPE: PRT
<213> ORGANISM: Mus musculus
```

```
<400> SEQUENCE: 7

Ser Ala Ser
1

<210> SEQ ID NO 8
<211> LENGTH: 9
<212> TYPE: PRT
<213> ORGANISM: Mus musculus

<400> SEQUENCE: 8

Gln Gln Tyr Ser Asn Tyr Pro Tyr Thr
1               5

<210> SEQ ID NO 9
<211> LENGTH: 351
<212> TYPE: DNA
<213> ORGANISM: Mus musculus

<400> SEQUENCE: 9
gaagtgaagc tggtggagtc tgggggaggt ttagtgcagc ctggagggtc cctgaaactc      60
tcctgtgcag cctctggatt cactttcagt agctatacca tgtcttgggt tcgccagact     120
ccagagaaga ggctggagtg ggtcgcatac attagtgatg gtggtggtgt cacctactat     180
ccagacacta taaagggccg attcaccatc tccagagaca atgccaagaa caccctgtac     240
ctgcaaatga gcagtctgaa gtctgaggac acggccatgt attactgtgc aagagatagg     300
tacggtctct ttgcttactg gggccaaggg actctggtca ctgtctctgc a              351

<210> SEQ ID NO 10
<211> LENGTH: 321
<212> TYPE: DNA
<213> ORGANISM: Mus musculus

<400> SEQUENCE: 10
gacattgtga tgacccagtc tcaaaaattc atgtccacat cagtaggaga cagggtcagc      60
atcacctgca aggccagtca gaatgtgggt attgctgtag cctggtatca acagaaacca     120
ggacaatctc ctaaactact gatttactcg gcatccaatc ggtacactgg agtccctgat     180
cgcttcacag gcagtggatc tgggacagat ttcactctca ccatcagcaa tatgcagtct     240
gaagacctgg cagattattt ctgccagcaa tatagcaact atccgtacac gttcggaggg     300
gggaccaagc tgaaataaaa c                                                321
```